United States Patent [19]

Brown et al.

[11] Patent Number: 4,666,430
[45] Date of Patent: May 19, 1987

[54] INFUSION PUMP

[75] Inventors: Eric W. Brown, Redondo Beach; Henry T. Tai, Pacific Palisades, both of Calif.

[73] Assignee: I-Flow Corporation, Torrance, Calif.

[21] Appl. No.: 677,849

[22] Filed: Dec. 5, 1984

[51] Int. Cl.⁴ .................................................. A61M 37/00
[52] U.S. Cl. ........................................ 604/141; 604/143; 604/249; 128/DIG. 12; 222/136; 222/399
[58] Field of Search ............... 604/141, 143, 147, 131, 604/140, 146, 173, 245, 65–71, 30, 31, 33, 154; 128/DIG. 12, DIG. 13; 251/118; 222/132, 136, 145, 399; 60/581, 591, 593

[56] References Cited

U.S. PATENT DOCUMENTS

| Re. 31,873 | 4/1985 | Howes | 604/43 |
|---|---|---|---|
| 1,541,615 | 6/1925 | Bessesen | 604/143 |
| 3,451,393 | 6/1969 | Sarnoff . | |
| 3,468,308 | 9/1969 | Bierman | 128/214 |
| 3,630,417 | 12/1971 | De Haas | 604/245 |
| 3,640,276 | 2/1972 | Dancy, Jr. | 128/214 |
| 3,640,277 | 2/1972 | Adelberg | 128/214 |
| 3,731,681 | 5/1973 | Blackshear et al. | 128/214 |
| 3,756,459 | 9/1973 | Bannister et al. | 604/65 |
| 3,895,741 | 7/1975 | Nugent | 222/103 |
| 4,043,332 | 8/1977 | Metcalf | 128/214 |
| 4,121,584 | 4/1978 | Turner et al. | 128/214 |
| 4,132,231 | 1/1979 | Puccio | 128/DIG. 12 |
| 4,140,117 | 2/1979 | Buckles et al. | 128/213 |
| 4,150,672 | 4/1979 | Whitney et al. | 128/214 |
| 4,196,730 | 4/1980 | Wilson | 128/214 |
| 4,221,219 | 9/1980 | Tucker | 128/260 |
| 4,265,241 | 5/1981 | Portner et al. | 128/260 |
| 4,274,407 | 6/1981 | Scarlett | 128/213 |
| 4,280,637 | 7/1981 | Runciman | 604/30 |
| 4,313,439 | 2/1982 | Babb et al. | 604/121 |
| 4,340,153 | 7/1982 | Spivey | 222/145 |
| 4,406,656 | 9/1983 | Hattler et al. | 604/43 |
| 4,421,508 | 12/1983 | Cohen | 604/70 |
| 4,430,078 | 2/1984 | Sprague | 604/141 |
| 4,505,701 | 3/1985 | Navato | 604/143 |
| 4,559,036 | 12/1985 | Wunsch | 604/81 |

Primary Examiner—Stephen C. Pellegrino
Assistant Examiner—Mario Costantino
Attorney, Agent, or Firm—Robert M. Asher

[57] ABSTRACT

An infusion pump is disclosed in which a canister of compressed gas is regulated to provide a continuous source of pressure to one or more compressible fluid sources. Valves on the outlets of the sources prevent fluid from escaping except when the valves are opened. The valves are opened by solenoids which are selectively activated to open the valves.

7 Claims, 7 Drawing Figures

INFUSION PUMP

BACKGROUND OF THE INVENTION

This invention relates to infusion pumps. There are many applications for which there is a need for a device which can intravenously administer a plurality of drug solutions. One such application is the use of chemotherapy to treat such diseases as cancer. Attempts at providing more advanced chemotherapy regimens involving the intravenous administration of a multiplicity of drug solutions are being inhibited by a lack of equipment to simplify such a procedure. Very often if different drug solutions are used, they are administered by using a separate catheter tube for each drug. A separate infusion pump would be used on each individual catheter tube line and the tube would deliver the fluid solution into the patient through its respective intravascular access needle. A patient must pay for each catheter set and must rent a pump for use with the catheter tube. Therefore, it is costly to use multiple catheter tubes and pumps.

Some physicians administer chemotherapy treatments with a plurality of drug solutions by mixing the solutions together and feeding the mixture into the patient through a single catheter set and pump. If the different drug solutions are compatible they can be mixed and delivered through a single catheter. Unfortunately, there are only a limited number of drug combinations which can be used in this manner. Many drugs cannot be mixed together prior to infusion. Some drugs react to neutralize one another. Other drugs react to form precipitates which may block the catheter tube or possibly cause an embolism in the patient.

It is desirable to provide a single pump that can deliver a multiplicity of drug solutions without mixing any of them prior to infusion. It is especially desirable for the pump to be lightweight so that it might be used on an ambulatory patient. U.S. Pat. No. 4,313,439 (Babb et al.) recognized the need for lightweight infusion pumps in a single drug delivery system. Babb et al. provided an escapement mechanism which applied a continuous pressure to a syringe. A constrictor acted on a catheter tube to prevent fluid from passing through the tube except during periods when the force from the constrictor was released to allow fluid through the tube.

SUMMARY OF THE INVENTION

This invention is directed to an infusion pump containing a compressible fluid source having an outlet which is normally blocked by a valve. A pressurized source of gas is fed through a pressure regulator and then against the fluid source to urge fluid against the valve. The valve may be opened to allow fluid to flow through the outlet.

The present invention is especially adapted for use with a plurality of compressible fluid sources. Control means are provided for selectively opening the valves to the sources. According to the present embodiment of the invention, a conduit is provided from the pressure regulator to the fluid source. The preferred sources are syringes. The syringes are sealed so that only the pressurized gas directed through the conduit is allowed into the tops of the syringes.

A disposable sterilizable valve of the present invention is connected to the bottom of each of the syringes. The valve of the present invention includes a hollow housing and a sealing member which is slidably mounted within a cylindrical bore inside the housing. The sealing member is connected to a plunger stem that has a T-shaped end which extends through a hollow slot in the bottom of the housing. A spring biases the sealing member away from the wall of the housing and into a closed position which prevents fluid from leaving through an outlet conduit in the side of the housing. The valve can be opened by pulling on the T-shaped end of the plunger stem. A flow restrictor is provided at the opposite end of the central bore to restrict the flow of fluid into the housing.

The pump of the present invention is light in weight since it is powered mostly by the pressurized gas. The only moving parts are the valves. This advantageously minimizes the chances of having any mechanical problems. Furthermore, this minimizes the need for electric power so that a very light battery package is sufficient to run the device. The construction of the present invention is easily adapted for use in multiple fluid infusions. The control means gives doctors a wide latitude in choosing their regimens, any of which may be programmed into the device.

Other objects and advantages of the invention will become apparent during the following description of the presently preferred embodiment of the invention, taken in conjunction with the drawings.

DETAILED DESCRIPTION OF THE PREFERRED EMBODIMENT

Figure 1:
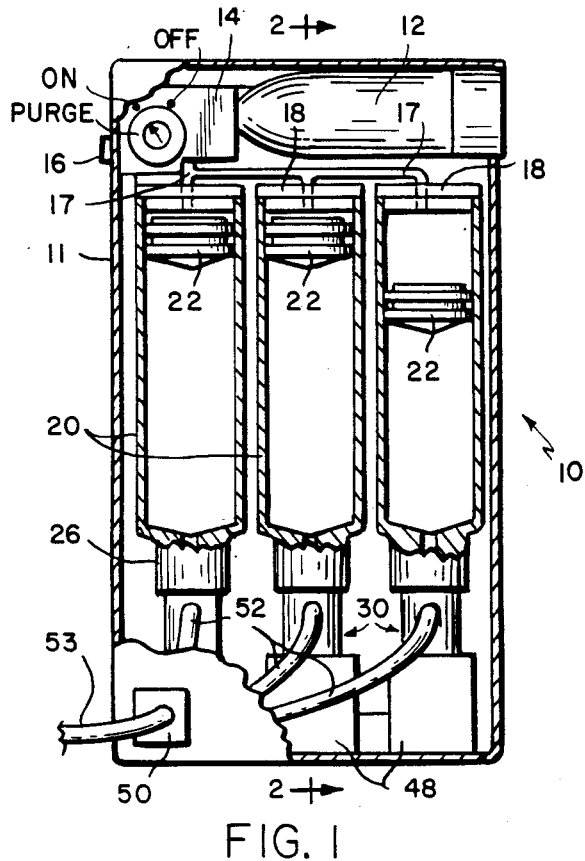
FIG. 1 is a substantially cut away view of the pump of the present invention.
Figure 2:
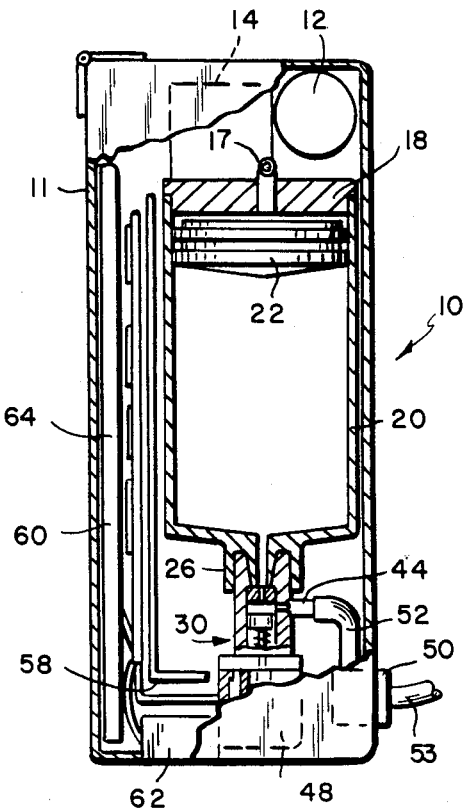
FIG. 2 is a cross-sectional view of the pump of FIG. 1 taken along lines 2—2.

Referring now to FIGS. 1 and 2, the infusion pump 10 of the present invention is illustrated. The pump is powered by a supply of compressed gas under high pressure. The supply is carried in canister 12. The canister may be replaced as needed to insure a supply of gas capable of pumping the contents of all of the fluid sources within the pump. The gas canister 12 is connected to a pressure regulator 14. The regulator 14 accepts the high pressure from the canister 12 and produces a continuous low pressure for use in the pump. The regulator 14 has a switch 15 which may be turned on, off, or to purge. In purge, the gas supply can be emptied through a pressure relief valve 16. The preferred embodiment is an ambulatory pump. For this purpose, the canister 12 is expected to be the most convenient source of a constant pressure. In a stationary device it may be possible to replace the canister with a central line that supplies a source of gas pressure. It may also be appropriate under certain circumstances to use mechanical means of providing a continuous source of pressure.

The gas pressure acts on a compressible fluid source to urge the fluid source out of its container. According to the preferred embodiment of the present invention, a syringe 20 such as that shown in FIGS. 3 and 4 may be used as the compressible fluid source. Such a syringe is described in a copending patent application entitled "SYRINGE" invented by Eric W. Brown and sharing the same assignee and filing date as the present application. Said patent application is hereby incorporated by reference within. The pump of the present invention is illustrated with three syringes. Obviously, the pump of the present invention may be constructed with any number of sources from as low as one to as high as would be medically useful.

Figure 3:
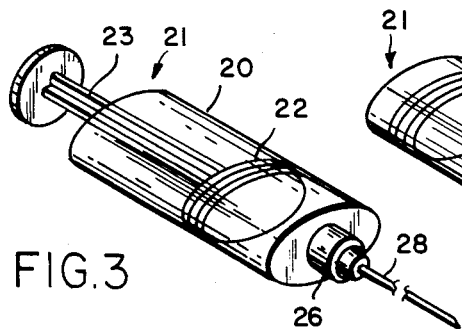
FIG. 3 is a perspective view of a syringe for use with the present invention.
Figure 4:
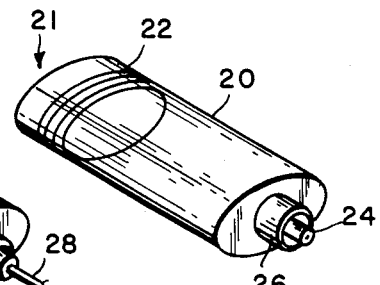
FIG. 4 is a perspective view of the syringe of FIG. 3 with its needle and plunger stem removed.

The described syringe 20 has an elliptical central bore 21 and an elliptical sealing member 22 which is slidable within that bore. A plunger stem 23 may be screwed into or out of the slidable member 22. To use the syringe 20 with the pump of the present invention, a conventional needle 28 is placed on the syringe tip 24 of the syringe 20. The plunger stem 23 at this time is screwed into the slidable member 22 as shown in FIG. 3. The slidable member 22 is pushed all the way against the wall of the syringe barrel and the needle 28 is poked into a desired fluid solution. The plunger stem 23 is pulled back to suck the fluid solution into the syringe 20. When the syringe contains the desired amount of solution, the plunger stem 23 is unscrewed from the slidable member and the needle is taken off the syringe tip 24. The syringe, as illustrated in FIG. 4, is now ready for use in the infusion pump. A syringe is used because it expels fluid upon being compressed. Any compressible fluid source may be used in place of the syringe. The syringe, however, is advantageously efficient in that it is capable of pushing out the entire fluid contents except for a very minor amount that might be left in the syringe tip.

Figure 7:
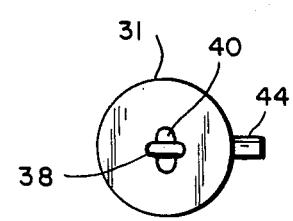
FIG. 7 is a bottom view of the valve of FIG. 5.
Figure 5:
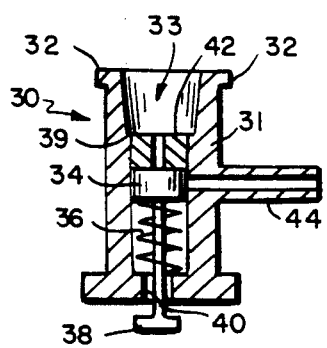
FIG. 5 is a cross-sectional view of the valve of the present invention in the closed position.
Figure 6:
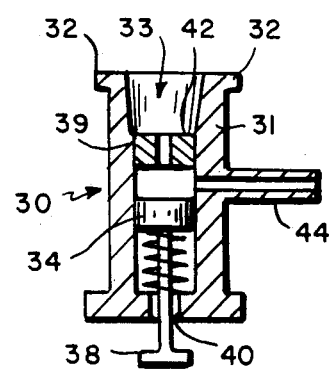
FIG. 6 is a cross-sectional view of the valve of FIG. 5 in the open position.

The syringe tip 24 is surrounded by a luer lock fitting 26. This is a standard male luer lock fitting that holds a conventional needle on the syringe. In the pump 10, a valve 30 is placed onto the syringe tip 24 of the syringe 20. The valve 30 is illustrated in FIGS. 5, 6, and 7. The valve controls the flow of fluid from its respective syringe 20. The valve 30 is normally closed to prevent fluid from escaping from the syringe 20 since the syringe is continuously under pressure while the pressure regulator 14 is on. A spring 36 within the valve 30 supplies the required pressure to hold the valve closed against the pressure exerted by the fluid from the syringe. Fluid is only allowed to leave the fluid source when the valve 30 is opened.

The valve 30 consists of a hollow housing 31. The valve 30 is made from sterilizable materials. Preferably, an inexpensive plastic material is used so that the valve is disposable. This allows total replacement of the syringes, valves and catheters with each use. By providing disposable valves the time consuming task of repeated sterilization is not required.

Tabs 32 extend from the valve housing 31 and serve as the female luer lock fitting. The tabs 32 engage the threads of the male luer lock fitting 26 so that the valve 30 may be screwed onto a syringe 20. The threads on the syringe 20 should be arranged so that the valve's outlet 44 points in the appropriate direction when the valve is screwed securely on the syringe. The valve 30 has a central bore 23 extending from an open end to a partially closed end of the housing 31. There is a ledge 39 in the central bore against which the syringe tip 24 will be held against when the valve is locked onto the syringe. At the partially closed end of the valve 30, a slot 40 provides an opening through the bottom wall of the housing 31. In construction of the valve, the spring 36 is inserted into the central bore 33. The spring 36 acts as the bias to force the valve normally closed. After the spring is inserted, a slidable sealing member 34 having a T-shaped plunger stem 38 is dropped through the central bore 33. The T-shaped stem 38 fits through the slot 40. Once it is through it may be turned 90° to help prevent it from falling back into the bore 33. The slidable member 34 provides a frictional seal against the walls of the central bore 33 to prevent fluid from leaking.

In the preferred embodiment, a flow restrictor 42 is inserted at the top of the valve 30. The flow restrictor 42 limits the flow of fluid through the valve 30 to a precise small amount. In this manner the amount of fluid solution being infused into a patient may be more accurately determined. As shown in FIG. 5, when the valve is closed the slidable member 34 is biased against the flow restrictor 42. In this position, the slidable member 34 blocks the fluid contents of the syringe from access to an outlet 44 which is provided in a side wall of the hollow housing 31. When the plunger stem 38 is retracted as in FIG. 6, fluid is allowed to flow through the flow restrictor 42, into the central bore 33 and out through the outlet 44. When the plunger stem 38 is released, the slidable sealing member pushes the fluid in the central bore out through outlet 44 and back through flow restrictor 42 until the valve is completely closed and the flow of fluid stops.

The syringe and their valves are accomodated in a pump housing 11. A rubber gasket 18 is connected to the pressure regulator 14 via conduit 17. The gasket 18 shown in FIG. 1 has three stopper-shaped seals for placement into the tops of the syringes 20. The conduit 17 may be three tubes connected together to carry the same pressure from the regulator 14. Alternatively, a single tube with three side outlet tubes may be used to connect the pressure regulator 14 to the three syringes 20. The conduit 17 is provided from the pressure regulator 14 to and through the centers of each of the stopper-shaped seals. The gasket 18 seals off each syringe 20 from the atmosphere. Each syringe 20 is subjected solely to the pressure provided from the regulator 14.

At the end of the housing opposite where the pressurized canister 12 and pressure regulator 14 are located, there are three solenoids 48. Any similarly functioning electromechanical device may be substituted for the solenoids 48. The movable core of the solenoid is provided with a clamp into which the plunger stem 38 of the valves may be snapped. When the solenoid 48 is energized the movable core is pulled downward, pulling the valve stem 38 with it to open the valve 30 and allow fluid to flow.

A catheter 52 is bonded in a conventional manner to the outlet 44 of each of the valves 30. According to the preferred embodiment, the other end of each catheter is fitted into a multilumen adapter 50. Any standard multilumen adapter may be used. The adapter connects each of the catheters 52 to a separate lumen in a multilumen catheter 53. The multilumen catheter 53 is connected to the adapter 50 for conducting fluids into the patient. It is preferred that the multilumen catheter be reinforced to prevent it from kinking. The preferred catheter set for use with the pump of the present invention is described in copending application entitled MULTILUMEN CATHETER SET sharing the same inventors, assignee and filing date as the present invention. The disclosure of said application is incorporated by reference herein. It is also possible to use separate single catheters from each of the fluid sources, however, this would require a separate intravascular access point for each tube, thereby becoming rather cumbersome and undesirable.

Each solenoid is connected to a printed circuit board 64. A control unit is provided on the circuit board 64. The control unit contains a microprocessor or other equivalent programmable controller for selectively activating the solenoids. The preferred ambulatory embodiment of the pump is provided with a flat lightweight battery package 60 which takes up a minimum amount of space and provides sufficient power to run the solenoids and the control circuitry. A shield 58 is provided to protect the electronic circuitry from any stray fluids. The shield 58 physically separates the electronic circuitry from the syringes. An interface 62 is also provided to allow the pump to interface with a programming device such as a computer or other dedicated programmer. It would also be possible but more cumbersome to provide the programming device within the pump unit itself.

In accordance with the present invention, a unique pump is provided for selectively pumping a plurality of fluid solutions into a catheter tube for infusion into a patient. It will be understood that the details of the control unit form no part of the present invention, except to the extent that it provides one commercially available programmable control means suitable for use in carrying out the steps required by the present invention, the programming techniques for adapting a microprocessor unit to such steps being well known in the microprocessor and programmable control means art.

The pump of the present invention may be programmed to provide fluids in any sequence, in any amount and at any time. The control unit is programmed to provide power to selected solenoids. The duration for which power is provided, the sequence of solenoid selection and the times at which power is provided may be programmed into the control. Pressure is continuously administered to all of the fluid sources. Fluid is infused only when a solenoid is energized to open a valve. The physician is thus given great flexibility in selecting an infusion regimen for a plurality of drug solutions.

The multilumen catheter connected to the pump may be readily attached to the patient using the multilumen catheter set described in the inventors' copending application. The pump may be carried by the patient for a couple of months. It is possible for a physician to regulate the administration of a drug regimen during the couple of months by programming the pump of the present invention. The patient will be provided with drug solutions at regularly prescribed intervals as preprogrammed by the physician over that period of time. The pump provides the patient with the freedom to leave his or her bed and still receive a complicated prescription involving more than one drug solution. Since electric power is only needed to periodically operate the solenoids, a small lightweight battery pack is sufficient. This contributes to the light weight of the pump which is especially beneficial to the patient's freedom of movement.

Of course, it should be understood that various changes and modifications to the preferred embodiment described above will be apparent to those skilled in the art. A switching mechanism might be placed near the pressure regulator to selectively provide pressure to selected syringes, thereby controlling delivery of fluid from the top end rather than the bottom at the valves. As already mentioned any type of compressible fluid source might be used in the present invention as well as any number of such sources. These and other changes can be made without departing from the spirit and scope of the invention and without diminishing its attendant advantages. It is therefore intended that such changes and modifications be covered by the following claims.

We claim:

1. An intravascular infusion pump comprising:

a source of pressurized gas;

a pressure regulator coupled to said gas source for providing gas at a lower pressure than that of the gas from said gas source;

a syringe having a barrel with an open end and a syringe tip at another end, said syringe barrel containing a fluid solution and having a slidable member which pushes the fluid solution out of the syringe through the tip when pressure is applied to the slidable member;

means for directing said pressurized gas from said pressure regulator to the open end of said syringe so that said gas exerts pressure directly on said slidable member to force fluid out through the tip of said syringe; and a valve coupled to the tip of said syringe, said valve including:

a housing having a passageway for fluid flow;

a sealing member slidably mounted within said passageway;

spring means for pushing said sealing member within said passageway to close off fluid flow through said valve;

means for moving said sealing member against the action of said springs means to open fluid flow through said valve; and flow restrictor means within said passageway to accurately limit the flow of fluid through said valve when said valve is open.

2. The intravascular infusion pump of claim 1, wherein said source of pressurized gas comprises a canister of compressed gas.

3. The intravascular infusion pump of claim 1 further comprising electromechanical means connected to said moving means of said valve for operating said moving means and control means coupled to said electromechanical means for selectively activating said electromechanical means.

4. The intravascular infusion pump of claim 1 wherein said means for directing said pressurized gas comprises a gasket for sealing the open end of said syringe and a conduit to provide a passage from said pressure regulator into the open end of said syringe.

5. The intravascular infusion pump of claim 1 wherein said means for moving said sealing member comprises a plunger stem connected to said sealing member at one end and having an other end extending out through said housing.

6. A multiple fluid infusion pump comprising:

a source of continuous pressure;

a plurality of compressible fluid sources each having an opening out through which fluid may flow;

means for directing pressure from said pressure source to said plurality of compressible fluid sources so as to continuously subject each fluid source to continuous pressure which urges fluid through the openings of said fluid sources;

a valve coupled to the opening in each of said plurality of fluid sources for controlling the flow of fluid from said source by preventing fluid flow when closed and allowing fluid flow when open, said valve including:

a housing having a passageway for fluid flow;

a sealing member slidably mounted within said passageway;

spring means for pushing said sealing member within said passageway to close off fluid flow through said valve;

means for moving said sealing member against the action of said spring means to open fluid flow through said valve; and flow restrictor means within said passageway to accurately limit the flow of fluid through said valve when said valve is open;

a multilumen adapter for receiving the fluid flow from each of said fluid sources through their respective valves and for separately feeding each fluid into one of a plurality of lumens in a multilumen catheter;

electromechanical means connected to each of said valves for opening and closing its respective valves; and control means coupled to each of said electromechanical means for selectively activating said electromechanical means.

7. The multiple fluid infusion pump of claim 6 wherein said means for moving said sealing member comprises a plunger stem connected to said sealing member at one end and having an other end extending out through said housing so as to be connected to said electromechanical means.

* * * * *